US005719151A

United States Patent [19]
Shall et al.

[11] Patent Number: 5,719,151
[45] Date of Patent: Feb. 17, 1998

[54] SUBSTITUTED BENZENE COMPOUNDS

[76] Inventors: Sydney Shall, 45, The Avenue, Lewes, East Sussex Bn10 1QT; Manoochehr Tavassoli, 87 Furzecroft Furze Hill, Brighton, East Sussex, BN3 1PE, both of Great Britain

[21] Appl. No.: 372,785

[22] Filed: Jan. 13, 1995

Related U.S. Application Data

[63] Continuation-in-part of Ser. No. 694,654, May 2, 1991, abandoned.

[30] Foreign Application Priority Data

May 4, 1990 [GB] United Kingdom ............... 9010129

[51] Int. Cl.$^6$ ............... A61K 31/54; A61K 31/535; C07D 403/00; C07D 403/02
[52] U.S. Cl. ............... 514/248; 544/237; 544/240; 544/63; 544/49; 544/285; 544/183; 544/68; 544/11; 514/647; 514/568; 514/309; 514/248; 514/230.5; 514/226.5; 514/259; 514/243; 564/163; 560/34; 546/142
[58] Field of Search ............... 514/248; 544/235, 544/237

[56] References Cited

U.S. PATENT DOCUMENTS

| | | | |
|---|---|---|---|
| 4,207,112 | 6/1980 | Ikenoue et al. | 430/566 |
| 4,623,662 | 11/1986 | DeVries | 514/596 |
| 4,835,268 | 5/1989 | Belanger et al. | 540/599 |
| 4,840,969 | 6/1989 | Tarnow et al. | 514/617 |
| 4,859,697 | 8/1989 | Ripka et al. | 514/438 |
| 4,861,778 | 8/1989 | Hall et al. | 514/248 |
| 4,994,490 | 2/1991 | Roy et al. | 514/522 |
| 5,032,617 | 7/1991 | Lee et al. | 514/617 |
| 5,324,839 | 6/1994 | Clemence et al. | 546/174 |

FOREIGN PATENT DOCUMENTS

| | | |
|---|---|---|
| 0 064 878 | 11/1982 | European Pat. Off. |
| 0 314 105 | 5/1989 | European Pat. Off. |
| 24 45 529 | 9/1974 | Germany. |
| 1 451 299 | 9/1976 | United Kingdom. |
| 2207425 | 2/1989 | United Kingdom. |

OTHER PUBLICATIONS

CA 108(19):167122b, JP 62223159 A (Oct. 1, 1987).
Abstract, JP 60152454 A (Aug. 10, 1985).
CA 102(25):220592j, JP 60019754 A (Jan. 31, 1985).
CA 84(1):4701m, JP 50004038 (Jan. 16, 1975).
Abstract, JP 74036220–B (Sep. 28, 1974).
Farzaneh, et al., Nucleic Acids Research, vol. 16, No. 23, pp. 11319–11326 (1988).
Nduka, et al, Eur. J. Biochem. 105, 525–530 (1980).
Durkacz, et al., Nature, vol. 283, No. 5747, pp. 593–596 (1980).
Shall, Adv. Rad. Biol. (1984) 11:1–69.
Cornellisen, et al., Biochem. Pharm. (1985) 34:4151–4156.
Oikawa, et al., Biochem. Biophys. Res. Commun (1980) 97:1131–1136.
Lindahl–Kiessling, et al., Carcinogenesis (1987) 8:1185–1188.
Farzaneh, et al., Nucleic Acids Research, (1990) 18:5981–5988.
Skidmore, et al., European Journal of Biochemistry (1979) 101:135–142.
Farzaneh, et al., Molecular and Biochemical Parasitology 14 (1985) 251–259.
**J. Labelled Compd. Radiopharm. vol. 22(6), pp. 623–630 (1985).
**Pharmazie vol. 33(10) p. 688 (1981).
**Izo. Akad. Nauk. SSSR. Ser. Khim vol. 10, pp. 2271–2275 (1971).
**Waldman et al., European Journal of Biochemistry (1979) 101:135–142.
Chemical Abstracts CA109(17):14203g (1988) — Registry No. 116591–63–0.
Chemical Abstracts CA109(17):142034g (1988) — Registry No. 58202–87–2.
Chemical Abstracts CA93(5):40248p (1980) — Registry No. 74182–38–0.
Chemical Abstracts CA93(5):40248p (1980) — Registry No. 58202–87–2.
Chemical Abstracts CA97(9):72722n (1981) — Registry No. 80913–77–5.
Chemistry Abstracts CA94(3):15921r (1980) — Registry No. 75918–49–9.
Chemical Abstracts CA94(3):15921r (1980) — Registry No. 75888–35–6.
Chemical Abstracts CA94(3):15921r (1980) — Registry No. 75664–78–7.
Chemical Abstracts CA112(21):191965g — Registry No. 116591–63–0 (1989).
Chemical Abstracts CA109(17):142034g — Registry No. 109737–27–1 (1988).
Chemical Abstracts CA107(9):77637y — Registry No. 109737–26–0 (1987).
Chemical Abstracts CA107(9):77637y — Registry No. 109737–14–6 (1987).
Chemical Abstracts CA107(9):77637y — Registry No. 87705–24–6 (1987).
Chemical Abstracts CA99(22):177488k — Registry No. 86478–97–9 (1982).
Chemical Abstracts CA99 (7):53390c — Registry No. 74182–38–0 (1982).
Chemical Abstracts CA93(5):40248p — Registry No. 67307–50–0 (1980).
Chemical Abstracts CA114(26):249130r — Registry No. 85126–66–5 (1990).

(List continued on next page.)

*Primary Examiner*—Matthew V. Grumbling
*Attorney, Agent, or Firm*—Zarley, McKee, Thomte, Voorhees, Sease

[57] ABSTRACT

Phthalazinedione compounds and pharmaceutical compositions are described. The compositions are useful in treating human or animal patients to alleviate or cure disease or disease symptoms caused by nuclear ADP-ribosyl and similar transferases.

12 Claims, No Drawings

OTHER PUBLICATIONS

Chemical Abstracts CA107(9):77637y — Registry No. 76888-19-2 (1987).

Chemical Abstracts CA94(15):121883q — Registry No. 50466-30-3 (1980).

Chemical Abstracts CA79(13):75344e — Registry No. 17090-31-2 (1973).

Chemical Abstracts CA106(5):32987a — Registry No. 17090-28-7 (1986).

Chemical Abstracts CA106(6):33506e — Registry No. 14056-15-6 (1986).

Chemical Abstracts CA94(2):9988b — Registry No. 7600-08-0 (1980).

Chemical Abstracts CA99(7):53390c — 22 registry numbers (all dealing with JP 58067657) (1982).

SUBSTITUTED BENZENE COMPOUNDS

CROSS-REFERENCE TO A RELATED APPLICATION

This application is a continuation-in-part of patent application Ser. No. 07/694,654 filed May 2, 1991, entitled "Novel Benzamides" now abandoned.

FIELD OF THE INVENTION

The present invention relates to substituted benzene compounds and, in particular, to substituted benzamides, typically for use in inhibiting ADP-ribosyl transferases such as those known as poly(ADP-ribose) polymerase or synthetase.

BACKGROUND OF THE INVENTION

The nuclei of all truly nucleated cells contain an enzyme which is generally known as poly(ADP-ribose) polymerase. The complete physiological function of this enzyme is not yet known, but published information indicates that it participates in DNA repair, DNA rearrangements, DNA transfection, and perhaps in many other reactions involving DNA.

A number of inhibitors of this enzyme have been described. Most inhibitors so far described have the general formula of an aromatic amide, namely:

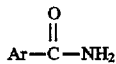

wherein Ar represents a monocyclic aromatic group, the amido group shown is bonded to a ring carbon atom of the aromatic group and Ar is either nnsubstituted (except by the amido group) or is substituted by at least one simple substituent atom or group compatible with the inhibitory activity.

The group Ar may also be heterocyclic (with one or two nitrogens in the ring) or dicyclic, with one heterocyclic ring containing up to two nitrogen atoms or a nitrogen and oxygen atom.

Examples of some important known inhibitors of poly (ADP-ribose) polymerase are:
Benzamide,
3-aminobenzamide,
3-bromobenzamide,
3-chlorobenzamide,
3-fluorobenzamide,
3-methylbenzamide,
3-methoxybenzamide,
3-hydroxybenzamide,
3-N-acetyl-aminobenzamide (3-acetamido benzamide)
3-N-propionyl aminobenzamide (3 propionamide benzamide)
Nicotinamide
5-methylnicotinamide
phthalhydrazide
3-aminophthalhydrazide (luminol or 5-amino-2,3-dihydro-1,4-phthalazinedione),
3-nitrophthalhydrazide,
Chlorthanoxazine,
Benzoylenurea, (2,4-[iH,3H] quinazolinedione)
Thymidine, and
Picolinamide.

The action of such inhibitors is known to be reversible, competitive and to prevent the depletion of intracellular NAD that is caused by DNA-damaging agents. Using such inhibitors, poly(ADP-Ribose)polymerase has been shown to be involved in DNA excision repair (Shall, S. (1984) Adv. Rad. Biol. 11, pages 1 to 69) and in the antigenic switching of *Trypanosoma brucei* (Cornelissen, A. W. C. A. et al. (1985) Biochem. Pharm. 34, pages 4151 to 4156). Inhibition of nuclear poly(ADP-Ribose)polymerase by 3-aminobenzamide has also been shown to generate a large increase in spontaneous sister chromatid exchanges (Oikawa, A. et al. (1980), Biochem. Biophys. Res. Commun. 97, pages 1131 to 1136, and Lindahl-Kiessling, K. & Shall, S. (1987) Carcinogenesis 8, pages 1185 to 1188). The latter two above-mentioned processes involve homologous DNA recombination.

Infection of mammalian cells by retro-viruses involves many steps. First there is an interaction between the viral envelope and specific host-cell receptors, then there follows entry of the viral particle and uncoating of the enveloped virion. This is followed by reverse transcription of the viral RNA genome by reverse transcriptase into the double-stranded proviral DNA.

After these steps there occurs the integration of a proportion of the proviral DNA molecules into the host cell chromosomal DNA. The integration step involves a coordinated set of DNA strand-breakage and rejoining events, which are catalyzed by a viral enzyme called integrase. When the integrase has completed its function, there apparently remains two single-strand nicks in the DNA; these nicks have to be repaired by the cell DNA repair enzymes. Inhibitors of poly (ADP-ribose)polymerase prevent correct DNA strand rejoining. Direct evidence that non-homologous DNA strand-rejoining of this type is blocked by inhibitors of poly (ADP-ribose) polymerase has been published.

Thus, it has recently been shown that the inhibition of poly(ADP-Ribose)polymerase by 3-methoxybenzamide or 3-aminobenzamide blocked the integration of foreign DNA into the genome during a calcium phosphate mediated DNA transfection procedure involving non-homologous/ illegitimate DNA recombination (Farzeneh, F. et al (1988) Nucleic Acids Research 16, pages 11319 to 11326). This inhibition was shown to be specific to the integration step of DNA transfection. The uptake and expression of foreign DNA (introduced via plasmids) was not affected. Reference is also made to Waldman, B. C. and Waldman, A. S. (1990). Illegitimate and homologous recombination in mammalian cells: differential sensitivity to an inhibitor of poly(ADP-ribosylation). Nucleic Acids Res. 18, 5981–5988.

From this data it can be concluded that the DNA repair step in the retroviral life-cycle will be blocked by such inhibitors and that these inhibitors would block the successful reproduction of these retroviruses.

Some poly(ADP-Ribose)polymerase inhibitors have found a role in cancer therapy. DNA damage such as strand breaks, base damage and cross-linking due to X-ray or bleomycin exposure during radio- or chemotherapy is reparable. The poly(ADP-Ribose)polymerase inhibitors 3-aminobenzamide and nicotinamide have been shown to inhibit recovery of the damaged cells, and 3-aminobenzamide seems to work by delaying the rejoining of broken DNA strands.

More specifically, radiation or chemical killing of cancer cells is an important aspect of the treatment of cancer patients. Inhibitors of poly(ADP-ribose)polymerase have been shown to potentiate the killing of mammalian cancer cells, both by radiation and by chemicals (Skidmore, C. J., Davies, M. I., Goodwyn, P. M., Halldorsson, H., Lewis, P. J., Shall, S., & Zia'ee. (1979) European Journal of Biochemistry. 101; 135–142). This original observation has been repeatedly confirmed. Furthermore, it has been demonstrated that the ability of a number of enzyme inhibitors to enhance killing by radiation correlates with their potency as inhibitors of poly(ADP-ribose)polymerase. In addition, it has been shown that this is true for compounds that are used clinically in the treatment of human patients. There are also reports of this effect using rodent animal models of cancer treatment. It is therefore now predictable that any newly described inhibitor of poly(ADP-ribose)polymerase would also potentiate the efficacy of both radiation and chemical killing of cancer cells.

In addition to poly(ADP-Ribose)polymerase, there are also other similar mono(ADP-Ribose) transferases which add mono ADP-Ribosyl groups onto specific aminoacid residues in various important cellular proteins. Furthermore, a number of important bacterial toxins are enzymes of this type.

SUMMARY OF THE INVENTION

Novel substituted benzene compounds and compositions containing the compounds are used for medicinal treatments such as a treatment for African trypanosomiasis. In other aspects of the invention such compounds are used medicinally for potentiating radiation or chemotherapy, etc.

DETAILED DESCRIPTION OF THE INVENTION

We have now found that certain other novel benzamides act as inhibitors of nuclear ADP-ribosyl and similar transferases and, thus, are useful in medicine, for example, in the treatment of retroviral diseases and African trypanosomiasis, as an adjuvant in cancer therapy or in certain cases of immune disease, or in the treatment of conditions caused by certain bacterial toxins. In addition, in view of their inhibitory activity it is thought possible that one or more of the said compounds may be useful in the treatment of patients infected with a human immunodeficiency virus (HIV). Furthermore, certain non-inhibitory chemical analogues of said novel benzamides are useful as intermediates and as controls in toxicity and other testing.

Accordingly, the present invention provides a method for the treatment of human or animal patients to alleviate or cure disease or disease symptoms caused by nuclear ADP-ribosyl and similar transferases, comprising administering an effective amount of a compound of the formula

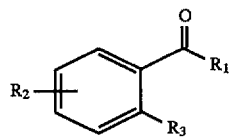

wherein:

$R_1$ is amino, substituted amino, hydroxy or alkoxy;

$R_3$ is hydrogen or together with $R_1$ is a group of the formula —Y—X—NH—, wherein Y is CO, COH, NH, O or S and X is CH$_2$, NH, N, CO, O or S, thus forming a ring; and $R_2$ is meta to the group —CO—$R_1$ when $R_1$ and $R_3$ are not conjoined, is at the 5- or 8- position when $R_1$ and $R_3$ are conjoined and is acylamino including alkenoylamino and haloacylamino; alkanolamino, haloalkylamino; a mercapto amino derivative, including thioalkylamino; substituted hydroxy, including alkylhydroxy, alkanolhydroxy, alkenylhydroxy, alkenoylhydroxy, or a mercapto hydroxy derivative, including thioalkylhydroxy; mercapto and substituted mercapto, including alkanolmercapto, acylmercapto, (including alkenoylmercapto) and haloalkylmercapto; guanidino or substituted guanidino; or ureido or substituted ureido, or, when $R_1$ and $R_3$ are together a group of the formula —Y—X—NH— is hydroxy, provided that when $R_1$ is amino and $R_3$ is hydrogen $R_2$ is not alkanoylamino containing 2 or more carbon atoms, carboxyalkanoylamino, aminoalkyanoylamino, oxoalkanoylamino or alkylhydroxy and that when $R_1$ is hydroxy and $R_3$ is not an aryl-containing acylamino group or an acylamino group containing conjugated double bonds.

The invention also provides pharmaceutical compositions comprising a pharmaceutically acceptable diluent or carrier and, as active agent, a said compound.

In another aspect, there are provided novel compounds of the formula:

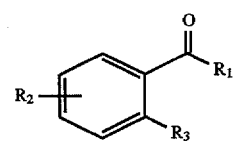

wherein:

$R_1$ is amino and $R_3$ is hydrogen; or $R_3$ together with $R_1$ is a group of the formula —Y—X—NH—, wherein Y is CO, COH, NH, O or S and X is CH$_2$, NH, N, CO, O or S, thus forming a ring; and $R_2$ is meta to the group —CO—$R_1$ when $R_1$ and $R_3$ are not conjoined, is at the 5- or 8- position when $R_1$ and $R_3$ are conjoined and is acylamino including alkenoylamino and haloacylamino; alkanolamino, haloalkylamino; a mercapto amino derivative, including thioalkylamino; substituted hydroxy, including alkylhydroxy, alkanolhydroxy, alkenylhydroxy, alkenoylhydroxy, or a mercapto hydroxy derivative, including thioalkylhydroxy; mercapto and substituted mercapto, including alkanolmercapto, acylmercapto (including alkenoylmercapto) and haloalkylmercapto; guanidino or substituted guanidino; or ureido or substituted ureido; or, when $R_1$ and $R_3$ are together a group of the formula —Y—X—NH—, is hydroxy; provided that, when $R_1$ is amino and $R_3$ is hydrogen, $R_2$ is not alkanoylamino containing 2 or more carbon atoms, carboxyalkanoylamino, aminoalkanoylamino, hydroxyalkoxyalkanoylamino, oxoalkanoylamino, ethenoylamino, haloacetylamino, alkylhydroxy, or aryl-containing acylamino, and provided that the compound is not 1,5 dihydroxy 3-hydro-4-phthalazinone, In the compounds of the invention $R_2$ is preferably a substituted amino group of the formula $R_4CZNH$— in which:

Z is oxygen, sulphur or NH;

$R_4$ is hydrogen, haloalkyl, alkenyl, amino or substituted amino (thus giving, for example, ureido and substituted ureido, as well as guanidino or substituted guanidino, depending on the value of Z); and $R_4$ is also alkyl when $R_1$ and $R_3$ are together a group of the formula —Y—X—N H—.

In the above preferred compounds of the invention Z is preferably oxygen. Also, $R_1$ and $R_3$ are together preferably a group of the formula

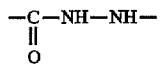

R₁ when it is substituted amino preferably may be mono-substituted and the substituent is preferably an alkyl group, more preferably an alkyl group having from about 1 to about 6 carbon atoms. Similarly, when R₁ is alkoxy the alkoxy group preferably contains from about 1 to about 6 carbon atoms and, more preferably, is ethoxy.

Most preferably, R₁ is amino, hydroxy or ethoxy or together with R₃ is a group of the formula —X—Y—NH—, thus giving a compound of the formula:

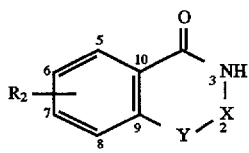

As to group R₄, that is preferably hydrogen, chloromethyl, bromomethyl, 3-chloropropyl, 3-bromopropyl, 2-chloropropyl, propenoyl (acryloyl), butenoyl (crotonyl), amino, methylamino or N-methyl, N-nitroso amino. That is to say, in other words, R₂ is preferably formylamino, chloroacetylamino, bromoacetylamino, 3-chloropropylamino, 3-bromopropylamino, 2-chloropropylamino, 3-propenoylamino, 3-butenoylamino, 3-ureido, 3-methylureido, or 3-N-methyl-N-nitroso-ureido.

Also, when R₁ and R₃ together form a ring, then R₂ is preferably:

hydroxy, formylamino, or acetylamino.

In the compounds of the invention as defined above the R₂ substituent is preferably in the meta position to the group —CO—R₁ when R₁ is not joined together with R₃. However, when R₁ and R₃ form a ring the preferred position of the substituent is position 5 or 8 in the lefthand ring.

In more preferred aspects of the invention the compounds of formula I above may be either a compound of the formula:

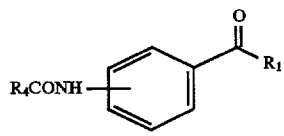

wherein R₁ and R₄ are as defined above or a compound of the formula:

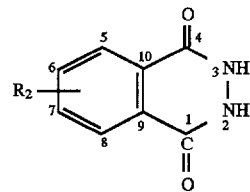

wherein R₂ is formylamino or acetylamino or hydroxy.

In compounds of the invention, especially those of formula III, the R4—CONH substituent is preferably in the meta position. As to compounds of formula IV, there the R₂ substituent is preferably in the 5- or 8- position.

The following new compounds have been synthesized and are especially preferred in accordance with the invention:

1) 3-formylaminobenzamide;
2) 2-formylaminobenzamide;
3) 4-formylaminobenzamide;
4) 3-propenoylaminobenzamide;
5) 2-propenoylaminobenzamide;
6) 4-propenoylaminobenzamide;
7) 3-N(3-chloropropyl)aminobenzamide;
8) 3-ureidobenzamide;
9) 3-methylureidobenzamide;
10) 4-methylureidobenzamide;
11) Ethyl-m-propenoylaminobenzoate;
12) 3-propenoylaminobenzoic acid;
13) 3-butenoylaminobenzamide;
14) 3-chloroacetylaminobenzamide;
15) 3-bromoacetylaminobenzamide;
16) 3-N(3'-bromopropyl)aminobenzamide;
17) 3-N(3'-chloropropyl)aminobenzoic acid;
18) Ethyl, 3-methylureidobenzoate;
19) 3(N-methyl,N-nitroso ureido)benzamide;
20) 4(N-methyl,N-nitroso ureido)benzamide;
21) Ethyl,3-(N-methyl,N-nitroso ureido)benzoate;
22) 3-formylamino-phthalhydrazide [N-formyl-luminol or 5-formylamino-2,3-dihydro- 1,4-phthalazinedione];
23) 4-formylamino-phthalhydrazide [N-formyl-isoluminol or 6-formylamino-2,3-dihydro- 1,4-phthalazinedione];
24) 3-acetylamino-phthalhydrazide [or 5-acetylamino-2,3-dihydro-1,4-phthalazinedione];
25) Ethyl-3-guanidinobenzoate;
26) 3-(guanidino)benzamide;
27) 1,5-dihydroxy-3-hydro-4-phthalazinone; and
28) 3(2-chloropropyl)aminobenzamide.

The compounds of the invention may be prepared by the following synthetic routes:

1. Compounds 1, 2, 3, 22 and 23 may be synthesized by formylation of the appropriate amide, with a mixture of formic acid and acetic anhydride (about 1) or by refluxing in formic acid.
2. Compounds 4, 5, 6, 7, 11, 12, 13, 16 and 17 may be synthesized by acylation of the appropriate amine and/or by the use of an appropriate acyl chloride derivative in acetone.
3. Compounds 14, 15 and 24 may be synthesized from the appropriate amine with acetic anhydride or with an appropriate acyl chloride derivative.
4. Compound 8 may be synthesized from 3-aminobenzamide and sodium cyanate in 33% acetic acid at 35° C.
5. Compounds 9, 10 and 18 may be synthesized by reacting the appropriate amine with methyl isocyanate.
6. Compounds 19, 20 and 21 may be synthesized by nitrosylation of the appropriate methyl ureido compounds, using sodium nitrite: the reactions occur in the solvents formic acid or dimethyl sulphoxide and sulphuric acid or in acetic anhydride.

7. Compounds 25 and 26 may be synthesized by refluxing 3-aminobenzamide hydrochloride with cyanimide in water. These compounds may also be made by refluxing 3-aminobenzamide and 2-methyl-2-thiopseudourea sulphate together in 30% ethanol.

8. Compound 27 may be synthesized by refluxing 3-hydroxyphthalic anhydride with hydraxine monohydrate in ethanol.

As indicated above the compounds of the invention are useful as inhibitors of ADP - ribosyl transferases. As such they are believed to be useful in the treatments set out above at levels ranging from 0.01 to 5 mmoles per kg. For example, at a level of about 0.02 mmoles per kg for compound 27 above.

Accordingly, the invention includes a pharmaceutical composition, which composition comprises a compound according to the invention and a pharmaceutically acceptable diluent or carrier.

The compositions of the invention may be formulated with solid or liquid diluents or carriers as is well known in the art. Furthermore, the formulated compositions may be put up in unit dosage forms such as tablets, capsules etc. as is also well known.

Some of the compounds of the invention act as reversible inhibitors in the same manner as known compounds. Surprisingly, however, certain of the compounds, in particular compounds 4 to 7, 11 to 17 and 19 to 21 are able to form covalent compounds. Moreover, compounds 4, 7, 14, 15, 16 and 19 exhibit a preferred feature in that they act by forming a covalent compound with the enzyme specifically and thus inhibit the enzyme. These are new and unexpected features.

In view of the above new and unexpected features, especially preferred compounds in accordance with the invention are those of the general formula III set out above, wherein $R_1$ is amino, hydroxy or alkoxy and $R_4$ is haloalkyl, alkenyl, or substituted amino.

More preferred compounds of the above formula are as follows:
3-propenoylaminobenzamide;
2-propenoylaminobenzamide;
4N(3-chloropropyl)aminobenzamide;
3-N(3-chloropropyl)aminobenzamide
Ethyl-m-propenoylaminobenzoate;
3-propenoylaminobenzoic acid;
3-butenoylaminobenzamide;
3-chloroacetylaminobenzamide;
3-bromoacetylaminobenzamide;
3-N(3'-bromopropyl)aminobenzamide;
3-N(3'-chloropropyl)aminobenzoic acid;
3-(N-methyl,N-nitroso ureido)benzamide;
4-(N-methyl,N-nitroso ureido)benzamide; and
Ethyl,3-(N-methyl,N-nitroso ureido)benzoate.

In the compounds of the invention the utility exhibited may be in terms of one or more of:
Inhibitory activity,
Utility as an intermediate, and/or
Utility as a control compound.

Generally speaking, the meta or 5- or 8- compounds defined or described above will exhibit inhibitory activity, whereas the ortho or para compounds (6- or 7- substituted compounds in the two ring compounds) may find better use as intermediates or controls. However, it may be the case that some of the ortho compounds also will exhibit useful inhibitory activity. Also, those compounds wherein $R_1$ is amino are good inhibitors, whereas those compounds wherein $R_1$ is other than amino are better used as intermediates and controls.

Moreover, the compounds which exhibit inhibitory activity are not necessarily those which form covalent compounds and vice versa. Thus, for example, compounds 12, 17, 20 and 21 form covalent compounds, but are not enzyme inhibitors.

The compounds and processes in accordance with the invention will now be illustrated by the following specific examples.

EXAMPLE 1

Synthesis of 3-formylaminobenzamide
(Compound 1)

A mixture of 40 ml of acetic anhydride and 40 ml of 98 to 100% formic acid was heated at 50° to 60° C. for 90 minutes. The solution was cooled to room temperature and 10 gm of 3-aminobenzamide was added in small aliquots over 15 minutes. The temperature was kept below 30° C. by occasional cooling in an ice-bath during the addition of the 3-aminobenzamide. The solution was stirred at room temperature for 2.5 hours, and then it was evaporated under vacuum to a viscous oil. Traces of acetic anhydride and of formic acid were removed by the repeated addition of water and evaporation until a white solid product was obtained. The solid product was crystallized from water. The white, round crystals were filtered off and washed with cold water and then dried under a vacuum. The overall yield was 78% and the melting point of the final material was 175° C. to 177° C. Mass spectrum analysis indicated a molecular weight of 164.

EXAMPLE 2

Synthesis of 3-formylaminobenzamide
(Compound 1)

10 gm of 3-aminobenzamide and 80 ml of 98 to 100% formic acid were refluxed for 60 minutes. The formic acid was removed by evaporation under vacuum; the residual oily product was mixed with water and evaporated to yield a solid residue. This solid was crystallized from water to give 8.2 gm (yield=68%) of white, round crystals with a melting point of 176° C. to 177° C. Mass spectrum analysis indicated a molecular weight of 164.

EXAMPLE 3

Synthesis of 2- and 4-formylaminobenzamide
(Compounds 2 and 3)

2- and 4(N-formylamino)benzamide were prepared by the method described in Example 2, except that the starting material was respectively 2- and 4-aminobenzamide.

EXAMPLE 4

Synthesis of 3-propenoylaminobenzamide
(Compound 4)

Propenoyl chloride from Aldrich Chemical Company Ltd. (2.2 gm, 24.3 mMole) was added dropwise to an ice-cold solution of 3-aminobenzamide (5.0 gm, 36.8 mMole) in 30 ml of acetone. The mixture was stirred on ice for 30 minutes, and then the white precipitate was filtered off and washed with cold acetone and then with cold water to give 4.2 gm of white product. The product was crystallized from 25% aqueous dimethyl sulphoxide and the crystallized product had a melting point of 229° C. to 230° C. The overall yield was 44%.

EXAMPLE 5

Synthesis of 3-propenoylaminobenzoic acid (Compound 12)

This was synthesized by a procedure similar to that used in Example 4 to give a product having a melting point of 247° C. to 248° C.

EXAMPLE 6

Synthesis of 20 and 4-propenoylaminobenzamides (Compounds 5 and 6)

These compounds were bynthesised in the same way as that used to make 3(N-propenoylamino)benzamide in Example 4, starting from 2- and 4-aminobenzamide. The observed melting points were: 2- compound 172° C. to 173° C. and 4-compound 254° C to 255° C.

EXAMPLE 7

Synthesis of 3-butenoylaminobenzamide (Compound 13)

This was achieved by the same procedure as that used to make 3-propenoylaminobenzamide, namely the route of Example 4, except that 2.30 gm (20 mMole) of butenoyl chloride was used. The product obtained had a melting point of 211° C. to 212° C.

EXAMPLE 8

Synthesis of Ethyl 3-propenoylaminobenzoate (Compound 11)

Propenoyl chloride (668 mg, 600 ul, 7.4 mMole) was added dropwise to an ice-cold solution of ethyl 3-aminobenzoate (2.0 gm, 12 mMole) in 10 ml of acetone. The solution was stirred for 30 minutes on ice and then for 30 minutes at room temperature. 50 ml of water was added and the yellowish oil was separated by decantation. It was washed with water and then dissolved in 15 ml of diethl ether. This solution was washed with 10% (w/v) sodium bicarbonate, water and then dried over anhydrous sodium carbonate. The ether was evaporated and a white creamy product was crystallized from ethanol. The overall yield was 37%, and the melting point of the product was 93° C. to 94° C.

EXAMPLE 9

Synthesis of 3-N (3-chloropropyl)aminobenzamide (Compound 7)

3-chloropropyl chloride (Lancaster Synthesis) (800 ul, 8.4 mMole) was added dropwise to an ice-cold solution of 3-aminobenzamide (1.5 gm, 11 mMole) in 15 ml of acetone. After stirring for 30 minutes on ice, the white precipitate was filtered off and washed with cold acetone and with water. Crystallization from 10% (v/v) ethanol yielded 1.1 gm of fine white needles; overall yield was 44%. The final product had a melting point of 188° C. to 189° C.

EXAMPLE 10

Synthesis of 3-N(3'-bromo propyl)aminobenzamide (Compound 16)

The same procedure as in Example 9 above was used except that 3-bromopropyl chloride was the reactant. The melting point of the product was 188° C to 189° C.

EXAMPLE 11

Synthesis of 3(2-chloropropyl)aminobenzamide (Compound 28)

The same procedure as in Example 9 above was used except that 2-chloropropyl was the reactant. The final product had a melting point of 193° C. to 194° C.

EXAMPLE 12

Synthesis of 3-ureidobenzamide (Compound 8)

Sodium cyanate (1.3 gm, 20 mMole) in 9.0 ml or water was added over a 15 minute period to a solution of 3-aminobenzamide (1.36 gm, 10 mMole) in acetic acid at 35° C. The mixture was stirred for a further 15 minutes during which time a white precipitate formed. This was filtered off, washed with cold water and crystallized from 25% ethanol to give 1.4 gm (78%) of shiny crystals. m.p. >300° C.

EXAMPLE 13

Synthesis of 3-methylureidobenzamide (Compound 9)

Methyl isocyanate (2.0 ml, 33.8 mMole) was added to a stirred solution of 3-aminobenzamide (4.5 gm, 33.0 mMole) in 40 ml of acetone. A white precipitate was formed in a few minutes; the reaction was continued with stirring for a further 30 minutes. The white precipitate was filtered off, washed with cold water and crystallized from 40% ethanol. Yield was 4.0 gm (62.5%); m.p. 230° C. to 231° C.

EXAMPLE 14

Synthesis of 3-formylamino-phthalhydrazide (Compound 22)

Process 1.

1.0 gm of 3-aminophthalhydrazide and 70.0 ml of 98% formic acid was refluxed for 60 minutes. The solution was cooled to room temperature and then to ice temperature. The precipitate was filtered off at 4° C., and washed with cold water. It was then dried under vacuum, giving 1.15 gm (99.0%) of a bright yellow product which was crystallized from dimethylsulphoxide. Melting point 293° C. to 294° C.

Process 2.

A mixture of 60 ml acetic anydyride and 60 ml of 98% formic acid was heated at 50° C. to 60° C. for 90 minutes. 1.0 gm of 3-amino phthalhydrazide was added to the warm solution (50° C.) with stirring. The reaction was then stirred at 37° C. for 3 hours. A yellow precipitate came out, which was cooled to 4° C. and filtered off. The product was washed with cold water and crystallized from dimethylsulphoxide. Process 1 gave a higher yield.

EXAMPLE 15

Synthesis of 1,5-dihydroxy-3-hydro-4-phthalazione (Compound 27)

3-hydroxyphthalic anhydride (1.0 gm, 6.1 mmole) was dissolved in 25 ml ethanol by heating and stirring. Hydrazine hydrate (0.315 ml, 6.5 mole) in 5 ml of ethanol was added dropwise to the clear solution. The mixture was refluxed in a water bath for 60 minutes, and was then cooled to 4° C. The precipitate was filtered off, washed with cold water, then with cold ethanol and dried under vacuum, giving 0.99 gm (90%) of white product, with a m.p. of 321 to 321° C. Crystallization from a water-ethanol mixture produced fine, white needle crystals with a m.p. of 329° to 331° C.

As will be appreciated, the invention is not limited to the specific details set out above by way of illustration only and numerous variations may be made within the spirit and scope of the claims which follow.

EXAMPLE 16

Determination of Inhibitory Effect

Methods

The enzyme activity was assayed by standard procedures (Murray, B. et al., Mutation Research (1986) 165:191–198). This reference also describes the estimation of the $K_m$ (Michaelis Constant) values. The estimation of the $K_i$ (inhibitory constant) values was performed by calculating the $K_m$ value in the presence or absence of known concentrations of the enzyme inhibitor. Standard biochemical calculations were then used to calculate the $K_i$ value. The smaller $K_i$ values indicate stronger inhibition. The degree of enzyme inhibition shown in the Table was estimated by measuring the enzyme activity in the presence and absence of the indicated concentrations of inhibitor. The in vitro inhibitory activity and Inhibition Constants $K_i$ for certain compounds are shown below:

TABLE 4

| COMPOUND | Concentration (µM) | Inhibitor Activity (%) |
|---|---|---|
| 1. 3-formylaminobenzamide | 5.0 | 66 |
| 2. 3-ureidobenzamide | 5.0 | 61 |
| 3. 3-methylureidobenzamide | 5.0 | 61 |
| 4. 3-guanidinobenzamide | 5.0 | 32 |
| 5. 5-formylamino-2,3-dihydro-1,4-phthalazinedione(5-N-formylluminol) | 1.0 | 54 |
|  | 2.5 | 71 |
| 6. 1,5-dihydroxy-3-hydro-4-phthalazinone | 1.0 | 47 |
|  | 2.5 | 71 |
|  | 5.0 | 82 |

Inhibition Constants of some poly (ADP-ribose)polymerase inhibitors are shown in Table 5.

TABLE 5

| Compound | $K_i$ (µM) |
|---|---|
| 1. 3-aminobenzamide | 11.3 ± 1.15 |
| 2. 3-acetylaminobenzamide | 3.20 ± 0.41 |
| 3. 3-propionylaminobenzamide | 2.49 ± 0.30 |
| 4. 3-formylaminobenzamide | 1.61 ± 0.15 |
| 5. 5-N-formylluminol | 0.518 ± 0.04 |

The $K_m$ for NAD, the substrate=100±13.7 µM, in the same assay.

The $K_i$ values shown in Table 5 show that the invention enables better inhibition of poly(ADP-ribose)polymerase than is obtainable with the prior art compounds 3-aminobenzamide, 3-acetylaminobenzamide and 3-propionylaminobenzamide.

EXAMPLE 17

3. Treatment of African Trypanosomiasis (African Sleeping Sickness)

African sleeping sickness is widespread in Africa, affecting both humans and domestic animals. In some parts of Africa it is a disease with a very high mortality, as well as a high morbidity among young adults. In addition, African sleeping sickness of commercial animals (called nagana, locally) is of tremendous economic importance because although much of Central Africa is ideal for ranching, nagana in the animals makes it non-economic. Consequently, there is an urgent need for a useful therapy of trypanosome infection of both humans and animals. African trypanosomes evade the host immune system by a process known as antigenic switching. In this process the parasites repeatedly change the antigens on their surfaces and thus evade destruction by the host immune system. We have shown in laboratory experiments that the inhibitors of poly (ADP-ribose) are able to slow down the antigenic switching by the parasites. These compounds then are potential candidates for therapy in both animals and humans affected by infection with African trypanosomes.

INVESTIGATION OF THE EFFECT OF NOVEL INHIBITORS OF THE ENZYME POLY(ADP-RIBOSE) POLYMERASE ON THE FREQUENCY OF ANTIGENIC SWITCHING IN TWO CLONES OF TRYPANOSOMA BRUCEI RHODESIENSE IN AXENIC CULTURE.

MATERIALS AND METHODS

1. TRYPANOSOMES: Stabilates of two clones, GUP 2889 and GUP 2814 were used.

Prior to propagation in vitro cell free culture conditions the parasites from stabilates were expanded in CD1 (8–9 week old) female mice. Infected mouse blood obtained by cardiac puncture in EMEM* with 20 U/ml heparin was used for the preparation of blood smears for immunofluorescence analysis.

2. ANTISERA AND MONOCLONAL ANTIBODIES (McAbs)

Specific rabbit antisera and ascites fluid against specific Variable Antigen Types were used for trypanolysis and immunofluorescence at the appropriate dilutions.

3. NEUTRALIZATION TRYPANOSOMES PRIOR TO AXENIC CULTURE

Antibody mediated lysis of a specific VAT of bloodstream form trypanosomes was performed by incubating an appropriate aliquot of a recently prepared trypanosome suspension at room temperature for 1 hour, in appropriately diluted specific antibody and guinea pig complement. The trypanosomes were observed and counted with inverted phase-contrast microscopy at a magnification of 150× to check for viability and to observe lysed trypanosomes, which appeared stumpy and vacuolated.

4. INITIATION OF AXENIC CULTURES

Cultures were initiated with aliquots of the above prepared trypanosome suspension. Duplicate T25 flasks, with 10 ml of medium were prepared for each experimental parameter examined. In each experiment the trypanosome density was determined at the initiation of the culture and at the end of the axenic culture period (usually after 18–24 hours) using a Neubaurer haemocytometer.

5. PREPARATION OF CULTURES TRYPANOSOMES FOR IMMUNOFLUORESCENCE

The prevalences of VATs in each cultures population were determined using immunofluorescence as follows: contents of one of the duplicate flasks (or both) were transferred to a universal bottle, and the trypanosomes were sedimented by centrifugation at 3,000 rpm at room temperature in a benchtop MSE centrifuge. The trypanosomes were resuspended in 10 µl of 20%(v/v) FCS supplemented EMEM* medium. Samples of this suspension were applied as smears to clean microscope slides coated with 0.1% poly-L-Lysine for immunofluorescence (IF) analysis for the frequency of specific VATs. Prevalence estimates of VATs were based on counts of more than 1000 labeled trypanosomes per flask.

6. IMMUNOFLUORESCENCE

Indirect immunofluorescence on acetone-fixed trypanosomes on slides was performed essentially according to the method of van Meirvenne et al., (Ann. Soc. Belge Med. Trop. (1975) 55: 1–23), using appropriately diluted rabbit antiserum or undiluted monoclonal lantibodies derived from hybridoma culture supernatants. Trypanosomes were visualized with fluorescein isothiocyanate(FITC)-labeled conjugated anti rabbit-FITC antibodies (Sigma:No.F-0382) for VAT 1.22 and 1.3, and with anti-mouse-FITC (Sigma:No.F-0257) for VATs 1.64c, 1.63a and 1.61. These secondary antibodies were diluted in PBS (pH8.0) and also contained Evans Blue (1:10,000 w/v) and Ethidium Bromide (5 µg/ml) as a counterstain.

Estimates of the prevalence of particular trypanosome VATs were based on counts of at least 200 trypanosomes, and at least 1000 trypanosomes were counted if the frequency of positive organisms were very low.

7. ESTIMATING THE RATE OF TRYPANOSOME VAT SWITCHING

The rate of switching was estimated essentially as described by Turner and Barry (Parasitology (1989) 99: 67–75). Briefly, the size of the trypanosome population expressing aminor VAT was calculated at the time points 11 and 12 as Nt1 and Nt2 respectively, from the mean total population density and from the prevalence of that VAT in the population.

The instantaneous rate of switching/cell/generation, σi, has been calculated. These values of σ are estimates of the per capita rate for switching to minor VATs. However, these estimates have been made in populations manipulated to consist of a major VAT, the prevalence of which is much higher than that of minor VATs; switching from minor to major VATs has therefore been assumed to be negligible, as has interswitching between minor VATs. Growth rates, r, have been expressed as population doubling times Td, where Td=loge2/r. Switching rates values are presented in the tables as finite, of, rate estimates.

8. INHIBITORS OF POLY(ADP-RIBOSE) POLYMERASE: 3-FORMYLBENZAMIDE AND 3-N-FORMYLLUMINOL (3-FORMYLAMINO-PHTHALHYDRAZIDE)

9. Design of Experiments:

Two clones of Trypanosoma brucei rhodesiense, GUP 2889 and GUP 2184 were initiated in culture with viable trypanosomes after in vitro trypanolysis of heterotype VAT 1.22 with GUPM 27.1 monoclonal antibody. Viable populations of these trypanosomes were incubated with various concentrations of the poly(ADP-Ribose)polymerase inhibitors. The effect of each concentration of inhibitor was tested in duplicate in T25 culture flasks set up for the axenic culture inhibition experiments. Growth was monitored after 24 hours of incubation at 37° C. in 4–5% $CO_2$ in air. Relative growth inhibition and frequency of antigenic switching of were calculated.

RESULTS

The estimation of antigenic switching frequency was based on the reappearance of detectable heterotypes, in an exponentially growing population in axenic culture. Prior to axenic culture, the specific heterotype was removed by complement-rich antibody trypanolysis. Although clone GUP 2889 was ideal in that the initial population was 90% homogeneous, it had a reduced propensity to switch to the detectable heterotype ILTat 1.22, 1.63, and 1.61. In contrast clone GUP 2814 (ILTat 1.63) which was 30% pure with a number of undetermined heterotypes which were not ILTat 1.61, 1.3 or 1.64, showed high switch rates, particularly the specific switch to ILTat 1.22.

Different concentrations of poly(ADP-Ribose) polymerase inhibitor were added to the culture medium in order to demonstrate their effect on growth and switching frequency in the two clones tested. In this assay a continuously growing bloodstream form trypanosome population was incubated in serial inhibitor dilutions in T25 culture flasks using an inoculum of $2\times10^4$-$1\times10^5$ trypanosomes per ml. After an incubation period of 24–48 hours in axenic culture at 37° C. in a 4–5% $CO_2$ incubator, trypanosomes were counted using a haemocytometer and growth inhibition was determined based on the number of generations (kt) of inhibitor treated cultures compared to controls. Table 6 shows that concentrations of 3-N-formylbenzamide ranging from 0.5 to 2.0 mM show a reduction in growth rate of 7%. Growth is reduced by up to 17% when 3-N-formylluminol (3-N-FL) is present in the concentration range of 50–400 μM, Table 7.

Table 3 shows data from inhibition experiments using 3-N-formylbenzamide (3FAB). Three separate experiments were carried out using 1 mM 3FAB, and in two of these where Horse Serum (Bristol) was used as supplement a reproducible reduction of switching frequency, from ILTat 1.63 to 1.22, was observed.

TABLE 6

THE EFFECT OF 3-FORMYL-AMINOBENZAMIDE(3FAB) ON THE GROWTH OF TRYPANOSOMA BRUCEI RHODESIENSE IN AXENIC CULTURE.

| Concentration of 3-formylaminobenzamide (3FAB) (mM) | Relative Growth Rate (S.D., n) |
|---|---|
| 0.0 | 1.00 |
| 0.5 | 1.05 ± 0.13, n = 6 |
| 1.0 | 1.03 ± 0.23, n = 11 |
| 2.0 | 0.93 ± 0.22, n = 6 |

TABLE 7

THE EFFECT OF 3-N-FORMYLLUMINOL(3-N-FL) ON THE GROWTH OF TRYPANOSOMA BRUCEI RHODESIENSE IN AXENIC CULTURE.

| Concentration of 3-N-Formylluminol(3-N-FL) (μM) | Relative Growth Rate (S.D., n) |
|---|---|
| 0.0 | 1.00 |
| 50 | 1.21 ± 0.13, n = 8 |
| 100 | 0.91 ± 0.22, n = 8 |
| 250 | 0.83 ± 0.42, n = 8 |
| 400 | 0.85 ± 0.04, n = 4 |

TABLE 8

THE EFFECT OF POLY(ADP-RIBOSE)POLYMERASE INHIBITOR -3- FORMYL AMINOBENZAMIDE(3FAB) ON ANTIGENIC SWITCHING IN TRYPANOSOMA BRUCEI RHODESIENSE(GUP 2814) IN AXENIC CULTURE.

Predominant homotype ILTat 1.63 (GUP 2814) and other unidentified heterotypes switching to ILTat 1.22.

| Culture System | Concentration of 3FAB(mM) | kt (doublings) | Relative Growth (%) | σf ($x10^{-2}$) | RAS (%) |
|---|---|---|---|---|---|
| ES/EMEM | 0.0 | 2.02 | 100 | 5.3 | 100 |
| | 1.0 | 1.56 | 77.2 | 2.26 | 42.6 |
| FCS/ EMEM | 0.0 | 2.143 | 100 | 0.46 | 100 |
| | 1.0 | 1.92 | 89.6 | 0.72 | 135.7 |
| ES/EMEM | 0.0 | 2.36 | 100 | 2.17 | 100 |
| | 1.0 | 2.14 | 90.8 | 0.94 | 43.5 |
| DHS/ EMEM | 0.0 | 2.44 | 100 | 210.8 | 100 |
| | 1.0 | 2.29 | 93.9 | 117.0 | 55.5 |
| ES/EMEM | 0.0 | 1.95 | 100 | 13.65 | 100 |
| | 0.5 | 2.09 | 107.2 | 0.95 | 7 |

In Table 8 "Culture System" refers to the axenic culture system as used; "ES" refers to horse serum prepared at Bristol, England (unprocessed); "DHS" refers to commercial donor horse serum supplied by Flow Laboratories; "FCS" refers to commercial foetal calf serum supplied by GIBCO; "EMEM" refers to supplemented eagle's minimum essential medium referred to previously as "EMEM"; "kt" refers to generation number; "σf" refers to finite switch rate per trypanosome per generation; "RAS" refers to relative antigenic switching; and finally, "VAT" refers to variable antigen type.

From all of the above examples 1–17 it can be seen that the invention accomplishes at least all of its stated objectives.

What is claimed is:

1. A pharmaceutical composition, comprising a pharmaceutically acceptable diluent or carrier and a poly (ADP-ribose)polymerase inhibiting effective amount compound of the general formula:

(I)

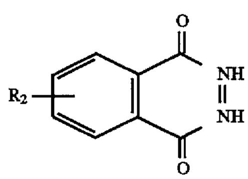

wherein:

$R_2$ is at the 5- or 8- position and is acylamino; hydroxyalkylamino, haloalkylamino; mercaptoalkylamino derivative, hydroxy or hydroxyalkyl; mercapto or mercapto alkyl guanidino or substituted guanidino; or ureido or substituted ureido.

2. A pharmaceutical composition according to claim 1 wherein the acylamino is alkenoylamino or haloacylamino.

3. A pharmaceutical composition according to claim 1 wherein the mercaptoalkylamino derivative is thioalkylamino.

4. A pharmaceutical composition according to claim 1 wherein the hydroxyalkyl is selected from the group consisting of alkylhydroxy, alkanolhydroxy, alkenylhydroxy, alkenoylhydroxy, and thioalkylhydroxy.

5. A pharmaceutical composition according to claim 1 wherein the mercapto alkyl is selected from the group consisting of alkanolmercapto, acylmercapto, and haloalkylmercapto.

6. A pharmaceutical composition according to claim 5 wherein the acylmercapto is alkenoylmercapto.

7. A pharmaceutical composition according to claim 1 wherein $R_2$ is selected from the group consisting of ureido, substituted ureido, guanidino, substituted guanidino and formylamino or acetylamino.

8. A pharmaceutical composition comprising a pharmaceutically acceptable diluent or carrier and a poly (ADP-ribose) polymerase inhibiting effective amount of a compound of the general formula:

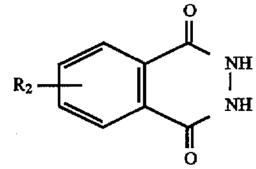

wherein $R_2$ is hydroxy or $R_4CONH$—, wherein $R_4$ is selected from the group consisting of hydrogen, alkyl, haloalkyl, alkenyl, amino and substituted amino.

9. A pharmaceutical composition according to claim 8 wherein $R_4$ is selected from the group consisting of hydrogen, alkyl, haloalkyl, and alkenyl and further providing that $R_2$ is at the 5- or 8- position.

10. A pharmaceutical composition according to claim 9 wherein $R_4$ is selected from the group consisting of hydrogen, alkyl and haloalkyl.

11. A pharmaceutical composition according to claim 10 wherein $R_4$ is hydrogen or alkyl.

12. A pharmaceutical composition in unit dosage form comprising a pharmaceutically acceptable diluent or carrier and a poly (ADP-ribose) polymerase inhibiting compound of the general formula:

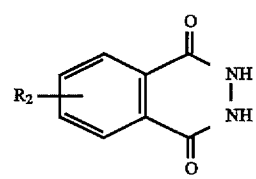

wherein $R_2$ is at the 5- or 8- position and is hydroxy or $R_4CONH$ wherein $R_4$ is selected from the group consisting of hydrogen, alkyl, haloalkyl and alkenyl.

* * * * *